United States Patent
Baniyash et al.

(10) Patent No.: US 10,914,743 B2
(45) Date of Patent: *Feb. 9, 2021

(54) KIT FOR DIAGNOSIS, PROGNOSIS, AND MONITORING THE IMMUNE STATUS, OF PATIENTS WITH CHRONIC INFLAMMATORY DISEASES

(71) Applicant: YISSUM RESEARCH DEVELOPMENT COMPANY OF THE HEBREW UNIVERSITY OF JERUSALEM, LTD., Jerusalem (IL)

(72) Inventors: Michal Baniyash, Mevaseret Zion (IL); Ilan Vaknin, Modiin (IL)

(73) Assignee: Yissum Research Development Company of the Hebrew University of Jerusalem, Jerusalem (IL)

(*) Notice: Subject to any disclaimer, the term of this patent is extended or adjusted under 35 U.S.C. 154(b) by 710 days.

This patent is subject to a terminal disclaimer.

(21) Appl. No.: 14/942,377

(22) Filed: Nov. 16, 2015

(65) Prior Publication Data
US 2016/0209424 A1    Jul. 21, 2016

Related U.S. Application Data

(62) Division of application No. 12/936,613, filed as application No. PCT/IL2009/000402 on Apr. 7, 2009, now Pat. No. 9,188,588.
(Continued)

(51) Int. Cl.
*G01N 33/68* (2006.01)
*G01N 33/569* (2006.01)

(52) U.S. Cl.
CPC ... *G01N 33/6872* (2013.01); *G01N 33/56972* (2013.01); *G01N 2333/7051* (2013.01);
(Continued)

(58) Field of Classification Search
CPC ......... G01N 33/6872; G01N 33/56972; G01N 2333/7051; G01N 2800/042;
(Continued)

(56) References Cited

U.S. PATENT DOCUMENTS

| 5,478,722 | A | 12/1995 | Caldwell |
| 6,194,207 | B1* | 2/2001 | Bell ..................... C12N 5/0636 424/93.71 |

(Continued)

FOREIGN PATENT DOCUMENTS

| WO | 2005/025310 A2 | 3/2005 |
| WO | WO 2005/025310 | * 4/2005 ........... A01K 67/027 |

OTHER PUBLICATIONS

Eleftheriadis et al. Chronic Inflammation and T cell Zeta-Chain Downregulation in Hemodialysis Patients Am J Nephrol 28 (152-157) 2008 (Published on-line Oct. 19, 2007).*
(Continued)

Primary Examiner — Gailene Gabel
(74) Attorney, Agent, or Firm — Mark David Torche; Patwrite Law

(57) ABSTRACT

Provided are methods and kits, e.g.; for testing the immune status of patients with chronic inflammatory diseases by measuring the TCR zeta chain (CD247) expression levels, and in particular a method and a kit for testing the selective downregulation of TCR zeta chain expression in T cells, NK cells, or NKT cells. Zeta chain expression is measured using antibodies directed against the intracellular zeta chain region, and these levels are compared with the expression levels of other T cell receptor subunits and NK cell markers. Provided are methods for determining diabetes complications in a diabetic patient. Further provided are kits for diagnosis, prognosis, and monitoring of same.

19 Claims, 10 Drawing Sheets

Related U.S. Application Data

(60) Provisional application No. 61/042,873, filed on Apr. 7, 2008.

(52) U.S. Cl.
CPC ............. *G01N 2333/70596* (2013.01); *G01N 2800/042* (2013.01); *G01N 2800/24* (2013.01); *G01N 2800/52* (2013.01)

(58) Field of Classification Search
CPC ..... G01N 2800/24; G01N 2333/70596; G01N 2800/52
See application file for complete search history.

(56) References Cited

U.S. PATENT DOCUMENTS

| | | | |
|---|---|---|---|
| 6,197,531 B1* | 3/2001 | Lieberman | G01N 33/56972 435/40.5 |
| 9,188,588 B2* | 11/2015 | Baniyash | G01N 33/56972 |
| 2011/0124017 A1 | 5/2011 | Baniyash | |

OTHER PUBLICATIONS

Eleftheriadis et al. Chronic Inflammation and T cell Zeta-Chain Downregulation in Hemodialysis Patients (Am J Nephrol 28 (152-157) 2008 (Published on-line Oct. 19, 2007). 28.

Healy et al. Impaired Expression and Function of Signal Transducing Zeta Chains in Peripheral T Cells and Natural Killer Cells in Patients with Prostate Cancer, Cytometry 32: 109-119 (1998).

Vaknin, et al., "A common pathway mediated through Toll-like receptors leads to T- and natural killer-cell immunosuppression", Blood, vol. 111, pp. 1437-1447, (2008).

Nanri, et al., "Impact of C-Reactive Protein on Disease Risk and Its Relation to Dietary Factors: Literature Review", Asian Pacific J Cancer Prey, vol. 8, pp. 167-177, (2007).

Tsirpanlis, "Inflammation in Atherosclerosis and Other Conditions: A Response to Danger", Kidney Blood Press Res, vol. 28, pp. 211-217, (2005).

Nakagomi, et al., "Decreased Expression of the Signal-transducing $\xi$ Chains in Tumor-infiltrating T-Cells and NK Cells of Patients with Colorectal Carcinoma", Cancer Research, vol. 53, pp. 5610-5612, (1993).

Eleftheriadis, et al., "Chronic Inflammation and T Cell Zeta-Chain Downregulation in Hemodialysis Patients", Am J Nephrol, vol. 28, pp. 152-157, (2008).

Schalkwijk, et al., "Plasma concentration of C-reactive protein is increased in Type I diabetic patients without clinical macroangiopathy and correlates with markers of endothelial dysfunction: evidence for chronic inflammation", Diabetologia, vol. 42, pp. 351-357, (1999).

Whiteside, "Down-regulation of c-chain expression in T cells: a biomarker of prognosis in cancer?", Cancer Immunol Immunother, vol. 53, pp. 865-878, (2004).

Eldor, et al., "Lipids and Glucose in Type 2 Diabetes: What About the p-Cell and the Mitochondria?", Diabetes Care, vol. 28, pp. 985-986, authors reply 987, (2005).

Boden, et al., "Lipids and Glucose in Type 2 Diabetes", Diabetes Care, vol. 27, No. 9, pp. 2253-2259, (2004).

Pickup, "Inflammation and Activated Innate Immunity in the Pathogenesis of Type 2 Diabetes", Diabetes Care, vol. 27, pp. 813-823, (2004).

Kuss, et al., "Clinical Significance of Decreased $\xi$ Chain Expression in Peripheral Blood Lymphocytes of Patients with Head and Neck Cancer", Clinical Cancer Research, vol. 5, pp. 329-334, (1999).

Eisenbarth, et al., "Islet and Pancreatic Transplantation—Autoimmunity and Alloimmunity", The New England Journal of Medicine, vol. 335, No. 12, pp. 888-889, (1996).

Schram, et al., "Markers of inflammation are cross-sectionally associated with microvascular complications and cardiovascular disease in type 1 diabetes—the EURODIAB Prospective Complications Study", Diabetologia, vol. 48, pp. 370-378, (2005).

Bronstein-Sitton, et al., "Sustained exposure to bacterial antigen induces interferon-γ-dependent T cell receptor $\xi$ down-regulation and impaired T cell function", Nature Immunology, vol. 4, No. 10, pp. 957-964, (2003).

Hotamisligil, "Inflammation and metabolic disorders", Nature, vol. 444, pp. 860-867, (2006).

Nambiar, et al., "Abnormal Expression of Various Molecular Forms and Distribution of T Cell Receptor $\xi$ Chain in Patients with Systemic Lupus Erythematosus", Arthritis & Rheumatism, vol. 46, No. 1, pp. 163-174, (2002).

Ezernitchi, et al., "TCR $\xi$ Down-Regulation under Chronic Inflammation Is Mediated by Myeloid Suppressor Cells Differentially Distributed between Various Lymphatic Organs", J Immunol, vol. 177, pp. 4763-4772, (2006).

Baniyash, "TCR $\xi$ Chain Downregulation: Curtailing an Excessive Inflammatory Immune Response", Nature Reviews: Immunology, vol. 4, pp. 675-687, (2004).

The International Search Report for International application No. PCT/IL2009/000402, dated Jun. 24, 2009, four pages.

Baniyash M. Down-regulation of the ICR chain $\xi$ curtailing an excessive inflammatory immune response. Invited review for Nat. Immunol. Rev. (2004) 4:675-687.

Bronstein-Sitton N., Cohen-Daniel L., Vaknin I., Ezernitchi A V., Leshem B., Halabi A., Houri-Hadad Y., Greenbaum E., Zakay-Rones Z., Shapira L., and Baniyash M. Sustained exposure to bacterial antigen induces IFNγ-dependent T cell antigen receptor zeta down-regulation and impaired T cell function. Nat. Immunol. (2003) 4:957-964.

Ezernitchi, A. V., Vaknin I, Cohen-Daniel, L., Levy, O., Halabi, A., Pikarsky, E., Shapira, L. And Baniyash, M. TCR zeta, down-regulation under chronic inflammation is mediated by myeloid suppressor cells differentially distributed between various lymphatic organs. J. Immunol. (2006) 177:4763-72.

Nambiar M P, Enyedy E J, Fisher C U, Krishnan S, Warke V G, Gilliland W R, Oglesby R J, Tsokos G C. Abnormal expression of various molecular forms and distribution of T cell receptor zeta chain in patients with systemic lupus erythematosus. Arthritis Rheum. (2002). 46:163-74.

Eleftheriadis T, Kartsios C, Yiannaki E, Kazila P, Antoniadi G, Liakopoulos V, Markala D. Chronic inflammation and T cell zeta-chain downregulation in hemodialysis patients. Am J Nephrol. (2008). 28:152-7.

Vaknin, I., Blinder, L., Wang, L., Gazit, R., Shapira, E., Genina, O., Pines, M. Pikarsky, E. and Baniyash M. A common pathway mediated through Toll-like receptors leads to T and natural killer cell immunosuppression. Blood (2008) 111:1437.

Kuss I, Saito T, Johnson J T, Whiteside T L. Clinical significance of decreased zeta chain expression in peripheral blood lymphocytes of patients with head and neck cancer. Clin Cancer Res. (1999) 5:329-34.

Hotamisligil S G, Inflammation and metabolic disorders. Nature (2006) 444:860-867.

International Search Report for International Application No. PCT/IL2009?oo0402, dated Jun. 24, 2009.

Nanri Aa, Moore M A, Kono S Impact of C-reactive protein on disease risk and its relation to dietary factors. Asian Pac J Cancer Prey. (2007) 8:167-77.

Eisenbarth, G. S. and M. Stegall, Islet and pancreatic transplantation-autoimmunity and alloimmunity N Engl J Med, (1996). 335: 888-90.

Boden, G. and M. Laakso, Lipids and glucose in type 2 diabetes: what is the cause and effect? Diabetes Care, (2004) 27:2253-9.

Eldor, R. and I. Raz, Lipids and glucose in type 2 diabetes: what about the beta-cell and the mitochondria?: response to Boden and Laakso. Diabetes Care (2005) 28:985-6; author reply 986-7.

Tsirpanlis, G., Inflammation in atherosclerosis and other conditions: a response to danger. Kidney Blood Press Res (2005) 28: 211-7.

Pickup, J. C., Inflammation and activated innate immunity in the pathogenesis of type 2 diabetes. Diabetes Care (2004) 27:813-23.

Schalkwijk, C. G., et al., Plasma concentration of C-reactive protein is increased in type I diabetic patients without clinical macroangiopathy

(56) References Cited

OTHER PUBLICATIONS and correlates with markers of endothelial dysfunction: evidence for chronic inflammation. Diabetologia, (1999) 42:351-7.

Schram, M. T., et al., Markers of inflammation are cross-sectionally associated with microvascular complications and cardiovascular disease in type 1 diabetes—the EURODIAB Prospective Complications Study. Diabetologia (2005) 18:370-8.

Nakagomi, et al., "Decreased Expression of the Signal-transducing Zeta-Chains in Tumor-inflitrating T-Cells and NK Cells of Patients with Colorectal Carcinoma," Cancer Research, vol. 53, pp. 5610-5612, (1993).

Whiteside, "Down-regulation of Zeta-Chain expression in T cells: a biomarker of prognosis in cancer," Cancer Immunol, Immunother, vol. 53, pp. 865-878, (2004).

\* cited by examiner

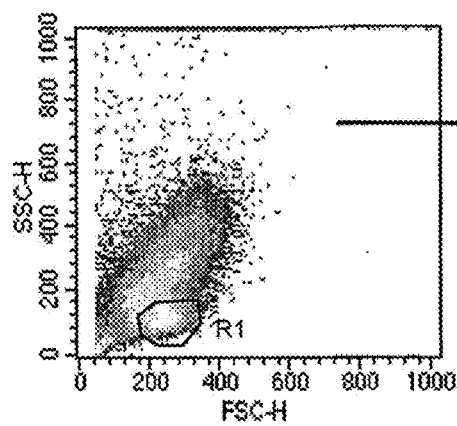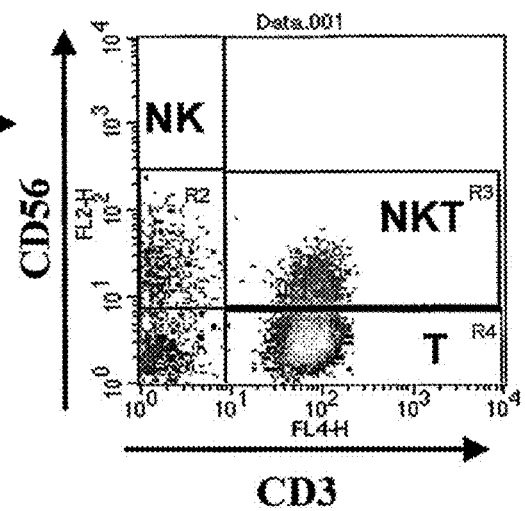
Fig. 1A            Fig. 1B
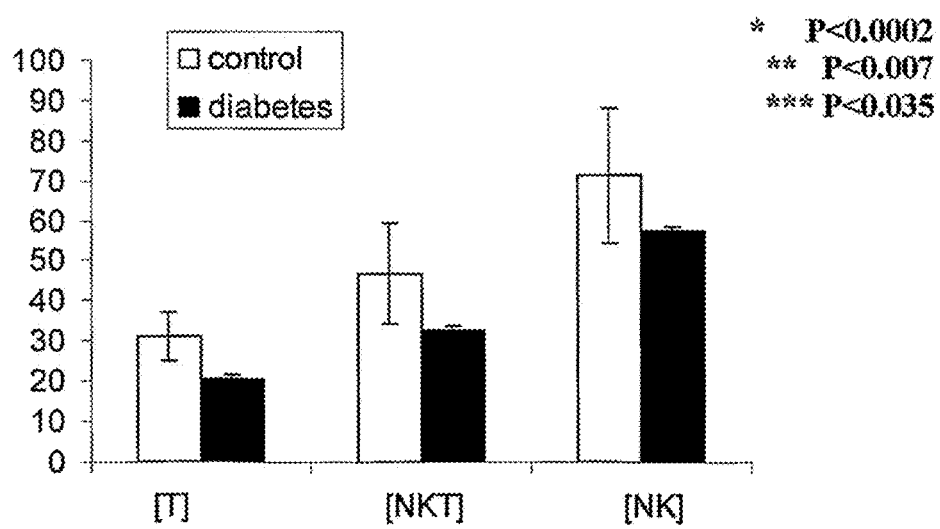
Fig. 1C

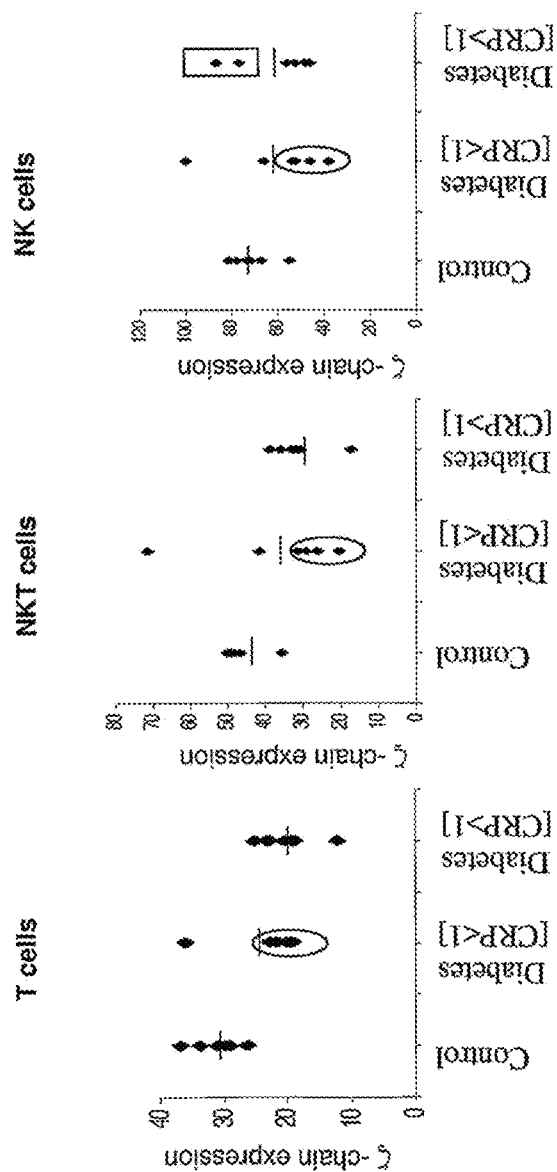

|  | CD247 (MFI) | CD3 (MFI) |
|---|---|---|
| Healthy donor 1 | 35.00 | 162.80 |
| Healthy donor 2 | 35.20 | 150.09 |
| Healthy donor 3 | 36 | 160 |
| Diabetic patient 1 | 19.60 | 160.84 |
| Diabetic patient 2 | 16.80 | 136.27 |
| Diabetic patient 3 | 17.00 | 145.99 |
| Diabetic patient 4 | 22.5 | 155.0 |
| Diabetic patient 5 | 32.8 | 170.0 |

KIT FOR DIAGNOSIS, PROGNOSIS, AND MONITORING THE IMMUNE STATUS, OF PATIENTS WITH CHRONIC INFLAMMATORY DISEASES

CROSS-REFERENCE TO RELATED APPLICATIONS

This application is a divisional application claiming benefit from U.S. patent application Ser. No. 12/1936,613 filed Jan. 31, 2011, now issued as U.S. Pat. No. 9,188,588 on Nov. 17, 2015, which is hereby incorporated in its entirety by reference.

FIELD OF THE INVENTION

The present invention concerns kits and methods for assessing immunosuppression in patients with chronic inflammatory diseases.

BACKGROUND OF THE INVENTION

The T cell receptor (TCR) complex consists of the clonotypic TCRα and β chains and the invariant CD3 γ, ε, ζ and chains, which are assembled in the endoplasmic reticulum and transported to the cell surface.

In various chronic pathologies such as cancer, autoimmune disorders and infectious diseases, partial or severe T lymphocyte and Natural Killer (NK) cell dysfunctions associated with a bystander down regulation of the ζ chain (CD247) was reported (reviewed in [1]). ζ chain is expressed in both T lymphocytes and NK cells as part of the T cell antigen receptor (TCR) and NK cytotoxic receptors (NCRs), respectively. In both cell types, the ζ chain has a key role in receptor assembly, expression and signaling function. The in vivo immunological mechanism underlying this phenomenon, which is observed as noted above in various diseases that largely differ in their etiology and physiology, was recently explored. It was shown that chronic inflammation is responsible for the induction of the bystander T and NK cell dysfunctions associated with ζ chain down regulation (2, 3 and 4). These studies revealed that low levels of ζ chain expression directly correlate with a chronic inflammation-dependent immunosuppressive environment. ζ chain down-regulation is not detected during acute inflammation. Moreover, elimination of the stimulus inducing the chronic inflammatory response leads to the recovery of ζ expression to normal levels.

Thus, ζ down regulation is a reversible event that depends upon the duration and severity of the inflammatory response. Our cumulative data led us to suggest that ζ chain down regulation could serve as a biomarker distinguishing between acute and chronic inflammation in patients suffering from diseases characterized by chronic inflammation and detects the ensuing immunosuppression. Moreover, due to its characteristics chain could serve as a biomarker for detecting the patient's immune status; an immunosuppressive immune system and its recovery, upon a given treatment that will induce neutralization of the immunosuppressive environment and thus, recovery of the immune function.

WO05025310 describes the use of ζ chain expression level as a marker for an immunosuppressive environment, wherein down regulation of TCR ζ chain expression indicates the presence of an immunosuppressive environment. This application mentions the immunosuppressive environment as being indicative of one of the following conditions: chronic inflammation, cancer, infections and autoimmune disorders. This application also mentions the use of ζ chain expression as a prognostic marker for the emergence of an immunosuppressive environment (as a predictive biomarker) for predicting the immune status in any of the above-mentioned conditions.

Various studies reported the detection of zeta chain expression in autoimmune disease patients or in cancer patients (6, 7) using either isolated T-cells or PBLs isolated on Ficoll gradient. In such samples T cells are isolated from the original immunosuppressive cells in the environment that could lead to zeta chain recovery and gain of immune function. Eleftheriadis et al (5) showed that zeta chain expression is downregulated in hemodialysis patients (HD) as compared to healthy subjects. In this study although both diabetic and non-diabetic HD patients were studied, the study emphasized the effects of HD on zeta chain expression and did not suggest involvement of zeta chain downregulation in non-HD diabetic patients.

The metabolic system and the immune system are among the most fundamental systems required for survival. Many metabolic and immune response pathways or nutrient- and pathogen-sensing systems have been evolutionarily conserved throughout species. As a result, immune response and metabolic regulation are highly integrated and the proper function of each is dependent on the other. This interface can be viewed as a central homeostatic mechanism, dysfunction of which can lead to a cluster of chronic metabolic disorders characterized by chronic inflammation, particularly obesity, diabetes and cardiovascular disease (8). Collectively, the risks and complications of these diseases constitute the greatest current threat to global human health and welfare.

Diabetes mellitus comprises a group of diseases that manifest hyperglycemia associated with end organ complications (9). Up to date, no linkage between chronic inflammation-induced immunosuppression and complication appearance in diabetes was made.

One of the major medical problems today of patients suffering from diabetes is the inability to predict complications prior to their diagnosis and there is a lack in parameters measuring competency of a given therapy. Currently, inflammation measurements rely mainly on CRP levels, blood sedimentation rates and levels of pro-inflammatory cytokines. However, since these compounds are elevated under both acute and chronic inflammation, neither of them can uniquely point at a chronic inflammatory state and therefore, most complications of diabetes patients are diagnosed only upon their occurrence (10, 11).

SUMMARY OF THE PRESENT INVENTION

By a first of its aspects, the present invention provides a kit for determining selective downregulation of chain (CD247) expression in a blood sample characterized in that it comprises:

(a) an antibody directed against an intra-cellular domain of the chain;

(b) at least one antibody directed against a CD3 subunit; and optionally (c) instructions for use.

In one embodiment, the kit is further characterized in that it comprises at least one additional antibody directed against a specific NK cell marker. In one embodiment of the invention the specific NK cell marker is CD56.

In one embodiment, the antibody directed against the intra-cellular domain of the chain is a monoclonal antibody (mAb). In one specific embodiment, said mAb is anti-CD247.

In one embodiment, the antibodies in the kit of the invention are labeled.

In one specific embodiment said antibodies are conjugated to a fluorescent label. Specifically, said antibody directed against the ζ chain is a fluorescently labeled anti-CD247 mAb.

The kit of the invention may further be characterized in that it comprises a labeled secondary antibody or a labeled reagent.

The kit of the invention may further be characterized in that it comprises a fixating agent and/or a permeabilization agent. In one embodiment, the fixating agent is selected from the group consisting of formaldehyde, glutaraldehyde, and paraformaldehyde.

In another embodiment the permeabilization agent is saponin or TRITON™ X-100 (POLYETHYLENE GLYCOL P-(1,1,3,3-TETRAMETHYLBUTYL)-PHENYL ETHER)

The kit of the invention may further be characterized in that it comprises fluorescent beads.

In another aspect, the present invention provides a method for determining selective downregulation of chain ζ expression in a blood sample, the method comprising:

(a) Obtaining a whole blood sample;
(b) Contacting the blood sample with a fixating agent thereby fixing the cells in the blood sample;
(c) permeabilizing said fixed cells;
(d) contacting the cells with antibodies directed against an intra-cellular domain of the ζ chain under conditions enabling antibody binding;
(e) contacting the cells with antibodies directed against at least one of the CD3 subunits, under conditions enabling antibody binding; and
(f) determining the level of antibody-protein complexes;

wherein a low level of chain ζ expression in the sample and a constant expression level of the at least one of the CD3 subunits is indicative of a selective downregulation of ζ chain expression.

In one embodiment, the method of the invention further comprises contacting said cells with at least one additional antibody directed against a specific NK cell marker. In one embodiment, said specific NK cell marker is CD56.

Steps (d) and (e) of the method of the invention may be reversed in order or performed simultaneously. In addition, in accordance with the invention, the step of contacting the cells with antibodies directed against at least one of the CD3 subunits and/or the at least one antibody directed against a specific NK cell marker is performed prior to fixing and/or prior to permeabilizing the cells.

In accordance with the invention the blood sample may be a fresh blood sample or a frozen blood sample.

In one embodiment, the fixating agent is selected from the group consisting of formaldehyde, glutaraldehyde, and paraformaldehyde.

In another embodiment, the permeabilization is performed using saponin or TRITON™ X-100 (POLYETHYLENE GLYCOL P-(1,1,3,3-TETRAMETHYLBUTYL)-PHENYL ETHER).

In one embodiment, the antibody directed against the intra-cellular domain of the ζ chain is a monoclonal antibody (mAb). In a specific embodiment, the mAb is anti-CD247. In another embodiment, the monoclonal antibody is fluorochrome-labeled.

In accordance with one embodiment of the invention the level of antibody-protein complex formation is detected using flow cytometry.

The method of the invention may be used in diagnosis, prognosis, evaluating the immune status or monitoring the effects of therapy in diseases characterized by chronic inflammation.

The method of the invention may also be used in diagnosis, prognosis, assessment of likelihood to develop disease-related complications or monitoring the effects of therapy in diabetic patients.

In another aspect, the present invention provides a method for detecting an immunosuppression status in a patient suffering from diabetes, the method comprising:

(a) determining the expression levels of ζ chain in cells in a blood sample obtained from said patient;
(b) determining the expression levels of at least one of the CD3 subunits in said cells; and
(b) comparing the level of expression to a standard expression level;

wherein a low level of ζ chain expression in the sample and a constant expression level of the at least one of the CD3 subunits is indicative of an immunosuppression status in the tested diabetic patient.

In another aspect, the present invention provides a method for predicting diabetes related complications in a patient, the method comprising:

(a) determining the expression levels of ζ chain in cells in a blood sample obtained from said patient;
(b) determining the expression levels of at least one of the CD3 subunits in said cells; and
(c) comparing the level of expression to a standard expression level;

wherein a low level of ζ chain expression in the sample and a constant expression level of the at least one of the CD3 subunits likelihood to develop diabetes-related complications.

In another aspect, the present invention provides a method for evaluating the efficacy of an anti-diabetes therapy the method comprising:

(a) Determining the expression levels of ζ chain in cells in blood samples obtained from said patient, wherein at least one of said blood samples is obtained before initiation of therapy and at least a second of said blood samples is obtained during therapy and/or after completion of therapy;
(b) Comparing the expression levels of ζ chain in cells in said blood samples; and
(c) Determining the expression levels of at least one of the CD3 subunits in said cells;

wherein an elevation in ζ expression level in the sample obtained during therapy and/or after completion of therapy as compared to the expression level in the sample obtained before therapy initiation, and a constant expression level of the at least one of the CD3 is indicative of successful therapy.

In one embodiment, the above methods of the invention further comprise determining the expression level of at least one specific NK cell marker. In one specific embodiment, said at least one specific NK cell marker is CD56.

BRIEF DESCRIPTION OF THE DRAWINGS

In order to understand the invention and to see how it may be carried out in practice, embodiments will now be described, by way of non-limiting example only, with reference to the accompanying drawings, in which:

FIG. 1 is a graphic representation of specific ζ-chain down-regulation in Type 2 diabetes patients. Whole blood from healthy and diabetic donors was stained for total ζ-chain, CD3, and CD56 expression levels.

In FIGS. 1 A and 1B, First, the lymphocyte population was gated based on physical properties such as size and granularity of the cells. Then the gating was performed on three lymphocyte subsets; NK, NKT and T cells as represented by R2, R3 and R4, respectively.

In FIG. 1C ζ-chain expression was measured by FACS as the mean fluorescent intensity (MFI) within each subpopulation.

FIG. 1 D illustrates T cells. FIG. 1E illustrates NKT cells. FIG. 1F illustrates NK cells.

FIG. 2 is a graphic representations of ζ-chain expression in Type 2 diabetes patients with normal or abnormal CRP levels. Whole blood from healthy donors and diabetic patients was stained for total ζ-chain, CD3, and CD56 expression levels and correlated with CRP levels.

FIGS. 2B, 2C and 2D) Distribution of ζ-chain expression in individual patients according the CRP levels. Each point represents the mean fluorescent intensity (MFI) of ζ-chain in individual donors as in FIG. 1A and grouped according to Type 2 diabetes patients with low CRP (n=6), high CRP (n=7) or healthy donors (n=6), the bar representing the mean. Four patients with normal CRP levels that are characterized by reduced ζ-chain expression are indicated (circled FIGS. 2B and 2C). Two patients with high CRP levels and show high ζ-chain expression levels are indicated (square box). (FIG. 2D)

(FIG. 3A) Total ζ-chain and CD3ε expression levels of gated T cells from healthy donor and Type 1 diabetes patient; Patient 1—a 21 year old female with recent onset type 1 diabetes and no diabetes related complications. (FIG. 3B) Total ζ-chain and CD3ε expression levels of gated T cells from healthy donor and type I diabetes patient; Patient 2—a 65 year old male with prolonged Type 1 diabetes and related nephropathy, retinopathy, neuropathy, cardiovascular disease and foot ulcers. (FIG. 3C) Whole fresh blood samples from healthy donors (controls) and patients exhibiting Type 1 diabetes with (n=2) or without (n=3) complications, which their onset is yet unknown to us (double blind test) were analyzed for total ζ and CD3ε expression levels by FACS.

FIG. 4 is a representations showing T cell dysfunction associated with abnormal ζ-chain expression in Type 2 diabetes patients.

In FIG. 4 T cells derived from whole blood of healthy donors and diabetic patients were analyzed for total ζ-chain (CD247) and CD3 expression levels by FACS; Mean Fluorescent Intensity (MFI) results are presented.

DETAILED DESCRIPTION OF THE PRESENT INVENTION

Figures 1D, 1E, 1F:
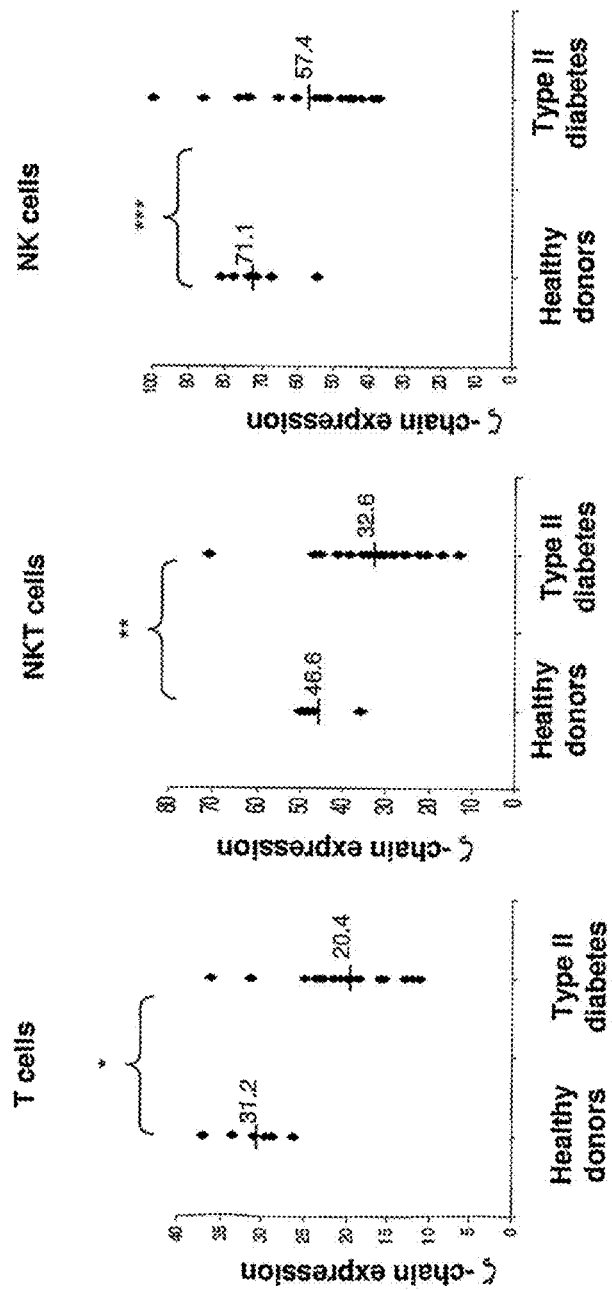
FIGS. 1D, 1E, and 1F Each point in the graph represents the mean fluorescent intensity (MFI) of the ζ-chain of the individual 20 type II diabetes patients or the 6 healthy donors analyzed in FIG. 1C, where the bar represents the mean value.

The present invention provides a sensitive and reliable method and kit for testing zeta chain expression, and in particular for testing the selective downregulation of zeta chain expression in T cells, NK cells, or NKT cells, in a patient's whole blood sample. ζ chain expression is measured using antibodies directed against the intracellular ζ chain region, which is accessible to antibodies in permeabilized cells.

The level of ζ chain expression, in combination with additional measured parameters (such as other TCR components and/or NK cell markers, e.g. CD56), serves as an indication of chronic inflammation-induced immunosuppression. Immunosuppression may be further verified using specific T cell functional tests.

The method of the invention can be performed with minute amounts of fresh or frozen blood samples. The use of frozen blood samples enables testing of zeta chain expression long periods of time (e.g. months) after the sample has been obtained. The ability to use frozen blood samples enables storage and accumulation of blood samples and allows to carry out the detection assays simultaneously on blood samples obtained from different patients and at different time points, thus, facilitating calibration of the results.

Thus, by a first of its aspects, the present invention concerns a method for determining selective downregulation of ζ chain expression in a blood sample, the method comprising:
(a) Obtaining a whole blood sample;
(b) Contacting the blood sample with a fixating agent thereby fixing the cells in the blood sample;
(c) Permeabilizing said fixed cells;
(d) Contacting the cells with antibodies directed against an intra-cellular domain of the ζ chain under conditions enabling antibody binding;
(e) Contacting the cells with antibodies directed against at least one of the CD3 subunits under conditions enabling antibody binding; and
(f) determining the level of antibody-protein complexes; wherein a low level of ζ chain expression in the sample and a constant expression level of the at least one of the CD3 subunits is indicative of a selective downregulation of ζ chain expression.

In one embodiment, the method further comprises contacting the cells with at least one additional antibody directed against a specific NK cell marker.

CD16 and CD56 are examples of typical NK cell markers. In one specific embodiment, said NK cell marker is CD56.

The blood sample may be fresh or frozen.

Cell fixation can be performed using any agent known to cause fixation of biological tissues. Examples of common fixating agents (also termed fixing agents) can be found, for example in the Sigma-Aldrich Catalog. See the Sigma-Aldrich Catalog available in print and online.

In one embodiment, said fixating agent is selected from the group consisting of formaldehyde, glutaraldehyde, and paraformaldehyde.

Permeabilization can be achieved by any manner that creates pores in the plasma membrane of the cells. Non-limiting examples include use of saponin or TRITON™ X-100 (POLYETHYLENE GLYCOL P-(1,1,3,3-TETRAMETHYLBUTYL)-PHENYL ETHER). The permeabilization enables the entry of antibodies into the fixed cells. Upon entry, such antibodies can react with intracytoplasmic domains of the ζ-chain.

In one embodiment said antibody is a monoclonal antibody (mAb) directed against the intracellular domain of ζ chain. In one specific embodiment said mAb is anti-CD247.

The binding of the antibody to the intracellular domain of the ζ chain can be determined by various techniques known in the art, for example by using a labeled anti ζ chain antibody and measuring directly the amount of the bound, labeled antibody. Alternatively, an unlabeled anti ζ chain antibody may be used followed by a secondary labeled antibody (e.g. labeled anti mouse, anti-rabbit or anti goat antibodies to be selected based on the type of the primary anti ζ chain antibody used in the assay). The level of binding is determined using methods well known in the art, for example Western blotting, radio-immunoassays, Elisa, or flow cytometry techniques.

In accordance with one embodiment of the invention the antibody is a fluorochrome-labeled monoclonal antibody (mAb) directed against the intracellular domain of ζ chain (CD247). In one specific embodiment said labeled mAb is anti-CD247.

In one embodiment, the binding is detected in a semi-quantitative manner using a flow cytometry assay.

In accordance with the invention, the antibodies against one of the CD3 subunit may be directed against an intracellular or an extracellular domain of one of the CD3 subunits.

In certain embodiments wherein antibodies against the extracellular domain of the CD3 subunit are used, said anti-CD3 subunit antibodies may be added prior to step (a), (the fixation of the sample), prior to step (b) (permeabilization of the cells) or during step (c) together with the anti-zeta chain antibodies.

In certain embodiments wherein antibodies against the intracellular domain of the CD3 subunit are used, said anti-CD3 subunit antibodies should be added during step (c) together with the anti-zeta chain antibodies.

In another embodiment, the method further comprises contacting the cells with at least one antibody directed against a specific NK marker. In one specific embodiment, said specific NK marker is CD56.

In certain embodiments said at least one antibody directed against the specific NK marker is added prior to step (a), (the fixation of the sample), prior to step (b) (permeabilization of the cells) or during step (c) together with the anti-zeta chain antibodies.

Monoclonal antibodies directed against CD247, CD3 subunits or NK cell markers are commercially available.

In another aspect, the present invention provides a kit for determining selective downregulation of ζ chain expression in a blood sample comprising:

(a) an antibody directed against an intra-cellular domain of the ζ chain; and (b) at least one antibody directed against a CD3 subunit; and optionally (c) instructions for use.

In one embodiment, the kit further comprises at least one additional antibody directed against a specific NK cell marker.

In one specific embodiment, said specific NK marker is CD56.

In one embodiment said antibody directed against the intra-cellular domain of the chain is a monoclonal antibody (mAb). In one specific embodiment said mAb is anti-CD247.

In one embodiment, the antibodies included in the kit (e.g. anti-CD247, anti-CD3 subunit and anti-CD56) are labeled antibodies.

In accordance with one embodiment of the invention the antibodies are labeled with a specific fluorochrome. In one specific embodiment, one of the antibodies is biotinylated and detected with a secondary fluorochrome-labeled reagent.

The following are non-limiting examples of labeling combinations for the antibodies:

anti-CD247-PE+anti-CD3-FITC+anti-CD56-Cy5/APC;
or
anti-CD247-FITC+anti-CD3-PE+anti-CD56-Cy5/APC;
or
anti-CD247-biot+anti-CD3-FITC+anti-CD56-Cy5/APC;
in this latter case if biotinylated antibodies are used, a secondary labeled reagent must be added, for example streptavidine-PE.

In another embodiment, the kit of the invention further comprises a labeled secondary antibody or a labeled reagent.

In one embodiment said kit further comprises a fixating agent and/or a permeabilization agent.

In one embodiment, said fixating agent is formaldehyde or paraformaldehyde.

In one embodiment, said permeabilization agent is saponin or TRITON™ X-100 (POLYETHYLENE GLYCOL P-(1,1,33-TETRAMETHYLBUTYL)-PHENYL ETHER).

In one embodiment, said kit further comprises fluorescent beads for calibrating the FACS before analysis of the cell staining and as a marker for a positive and negative fluorochrome staining.

The combined use of antibodies directed against CD3 subunits and an NK cell marker (e.g. CD56) allows to distinguish between different lymphocyte subpopulations in the blood sample, such as CD3+CD56− (T cells), CD3+CD56+ natural killer T cells (NKT cells) and CD56+CD3− (NK cells), thereby providing important information regarding the zeta chain expression levels in each of these subpopulations.

The method and kit of the invention may be used for diagnosis, prognosis, or monitoring the effects of therapy in a variety of diseases characterized by chronic inflammation and thereby serve as a general tool for the detection of an immunosuppressed status.

The present invention is based in part on the finding that patients suffering from a metabolic disease e.g. diabetes undergo changes in their immune status resulting in immunosuppression. Immunosuppression may be responsible for the onset of various diabetes-associated complications, and at least in part, for the deterioration in the patients' health condition. In accordance with the invention, ζ chain was used as a biomarker for the evaluation of the immune status of Type I and Type II diabetes patients exhibiting different stages of the disease.

Diabetes mellitus comprises a group of diseases that manifest hyperglycemia associated with end organ complications (9). The most common forms of diabetes mellitus are Type 1 and Type 2 diabetes. Type 1 diabetes is an autoimmune disease with immune mediated destruction of the insulin producing β cells (leading to complete insulin deficiency). Though originating in an autoimmune process, once a large portion of β cells have been destroyed (at the initial stages of the disease), the disease phenotype changes to a metabolic one, with chronically elevated levels of blood glucose and the resultant complications (12). Type 2 diabetes is an outcome of two parallel pathologic processes: end organ insulin resistance (especially in fat, muscle and liver tissue) and β cell dysfunction or death, leading to elevated blood glucose levels (13, 14). This disease was once called an adult-onset diabetes. However, in the Western countries, due to the epidemic of obesity and inactivity in children, Type 2 diabetes occurs at younger ages.

Both diabetes Type I and diabetes Type II can result in acute complications (ketoacidosis that results from insulin deficiency or hyperosmolar state as a result of elevated blood glucose levels) or in chronic complications associated with increased inflammation that affect many organ systems and are the major cause of morbidity and mortality in these diseases (4, 14). These late complications result in vascular injury that may take place in small arteries leading to diabetes associated retinopathy, nephropathy or in large arteries resulting in cardiovascular and cerebrovascular disease. Such vascular complications are thought to be at least partially a result of enhanced atherosclerosis and plaque formation in the vessel wall, a process undoubtedly associated with increased inflammation (14). Diabetes mellitus is also associated with immunosuppression manifested by prolonged wound healing and a greater frequency and severity of common and rare infections (15). Indeed patients suffering from diabetes have elevated markers of systemic inflammation, such as C-reactive protein (CRP), pro-inflammatory cytokines e.g. IL-6 and IL-1β, Plasminogen activator inhibitor 1 (PAI-1) and fibrinogen (9, 16-18).

However, these criteria cannot distinguish between acute and chronic inflammation and thus, are limited as a tool for detecting immunosuppression which results from chronic inflammation.

Presently, the diagnosis of diabetic complications can only be made after tissue damage is already apparent. Therefore, a sensitive biomarker that can predict the occurrence of disease-associated complications before they are evident is highly needed.

The method and kit of the invention can be used to evaluate the immune status (chronic inflammation-dependent immunosuppression) of the diabetic patient, and thus it can be used for predicting the onset of disease complications and also for monitoring the effects of therapy.

The method and kit of the present invention enable the physician to detect the presence of an immunosuppressed environment in patients suffering from metabolic diseases, evaluate the severity of the patient's immune status (immunosuppression), chose the appropriate therapeutic regimen and monitor the success of the treatment by determining at least one parameter indicative of an abnormal T-cell function preferably by determining zeta expression levels.

In such cases, where an immunosuppressed environment is observed the initiation of a therapy to neutralize the inflammation and the immunosuppression should be considered by the physician, even before the onset of diabetes-associated complications. Moreover, based on the characteristics of the ζ chain, it could be used as a biomarker for evaluating the competence of a given therapy that should neutralize the inflammation and the associated immune suppression and thus, enable an intelligent selection of the timing and therapy to be used. Moreover, the test for ζ expression requires a minute blood sample and is based on a simple and reliable FACS-based analysis. Thus, testing such a biomarker in a routine checkup basis of diabetes patients should be easy to perform and informative.

CRP is presently used as a marker for evaluating systemic inflammation. As proposed herein, the down-regulation of ζ chain expression may serve as a better marker for assessing chronic inflammation-induced immunosuppression in diabetic patients. The inventors discovered that there is no correlation between chain ζ expression and CRP levels; in some patients with high levels of CRP, ζ expression levels were normal while in other patients with normal CRP ζ expression levels were low. Moreover, since elevated CRP levels could not distinguish between acute and chronic inflammation and due to the critical role of the zeta chain in the immune function of T cells as well as of NKT and NK cells, the clinical value of measuring zeta expression levels is of great significance.

Accordingly, the present invention concerns by one of its aspects a method for detecting an immunosuppression status in a patient suffering from a metabolic disease, the method comprising determining at least one parameter indicative of T-cell abnormal function in a blood sample obtained from said subject; wherein a change in the parameter in a direction that is linked to abnormal T-cell activity is indicative of an immunosuppression status of the metabolic disease patient.

By another aspect, the present invention concerns a method for predicting metabolic-disease related complications in a patient the method comprising determining at least one parameter indicative of T-cell abnormal function in a blood sample obtained from said subject; wherein a change in the parameter in a direction that is linked to abnormal T-cell activity is predictive of an increased likelihood to develop metabolic disease-related complications.

Upon determination of likelihood to develop metabolic disease-related complications, a patient can benefit from an appropriate therapy.

By yet another aspect the present invention provides a method for monitoring the efficacy of therapy in preventing or reducing metabolic disease-associated complications in a patient, the method comprising determining at least one parameter indicative of T-cell abnormal function in a blood sample obtained from said subject; wherein a decrease in abnormal T-cell activity is indicative of a successful therapy.

Therapy may include, but is not limited to, pharmaceutical intervention including administration of drugs affecting the chronic inflammatory state, such as drugs that decrease LDL levels or anti-inflammatory drugs such as statins or aspirin, life style interventions such as diet or exercise, surgery (e.g. gastric bypass) or cell-based interventions (e.g. cell grafting or stem cell administration).

Various parameters may be measured as an indication of an abnormal T-cell activity, including, but not limited to:

1) ζ expression level—wherein a decrease in the level of ζ chain expression indicates immunosuppression;

2) Proliferation of T cells upon activation via the TCR wherein decreased proliferation indicates immunosuppression;

3) Expression level of various T-cell activation markers, such as CD25, and CD69 wherein decrease in the expression level indicates immunosuppression;

4) Level of cytokine production by T-cells upon T-cell activation, e.g. production of IL2, IFNγ, TNFα or IL6, wherein decreased cytokine production levels indicates immunosuppression.

In one embodiment, said metabolic disease is diabetes. In one specific embodiment, the present invention concerns a method for detecting an immunosuppression status in a patient suffering from diabetes, the method comprising:

(a) determining the expression levels of ζ chain in cells in a blood sample obtained from said patient;

(b) determining the expression levels of at least one of the CD3 subunits in said cells; and (c) comparing the level of expression to a standard expression level; wherein a low level of ζ chain expression in the sample and a constant expression level of the at least one of the CD3 subunits is indicative of an immunosuppression status in the tested diabetic patient.

In one embodiment, the method further comprises contacting the cells with at least one additional antibody directed against a specific NK cell marker.

In one specific embodiment, said specific NK marker is CD56.

In another specific embodiment, the present invention concerns a method for predicting diabetes related complications in a patient, the method comprising:

(a) Determining the expression levels of chain in cells in a blood sample obtained from said patient;

(b) determining the expression levels of at least one of the CD3 subunits in said cells; and (c) Comparing the level of expression to a standard expression level;

wherein a low ζ expression level in the sample as compared to the standard expression level while the level of expression of the at least one of the CD3 subunits remains unchanged is predictive of an increased likelihood to develop diabetes-related complications.

In one embodiment, the method further comprises contacting the cells with at least one additional antibody directed against a specific NK cell marker.

In one specific embodiment, said specific NK marker is CD56.

In accordance with one embodiment of the invention the standard expression level is represented by the expression level of ζ chain, CD3 subunit or CD56 in healthy human subjects. For example, the expression level is measured in a plurality of normal (healthy) tested human subjects and the ratio between ζ expression levels in T cells (representing maximum expression) versus the background staining in non-T cells of the same sample is evaluated, and determined as the standard.

In another embodiment the ζ chain, CD3 subunit or CD56 expression levels are compared to a standard expression level represented by fluorescent beads having a fluorescence level that equals the standard expression level of each of ζ chain, CD3 subunit and CD56 in a healthy subject.

In another specific embodiment, the present invention concerns a method for evaluating the efficacy of an anti-diabetes therapy the method comprising:

(a) Determining the expression levels of ζ chain in cells in blood samples obtained from said patient, wherein at least one of said blood samples is obtained before initiation of therapy and at least a second of said blood samples is obtained during therapy and/or after completion of therapy;

(b) Comparing the expression levels of ζ chain in cells in said blood samples; and (c) Determining the expression levels of at least one of the CD3 subunits in said cells; wherein a significant elevation in expression level in the sample obtained during therapy and/or after completion of therapy as compared to the expression level in the sample obtained before therapy initiation, while the level of expression of the at least one of the CD3 subunits remains unchanged is indicative of a successful therapy.

In one embodiment, the method further comprises contacting the cells with at least one additional antibody directed against a specific NK cell marker.

In one specific embodiment, said specific NK marker is CD56.

In one specific embodiment, the diabetic patients are not hemodialysis diabetic patients, namely diabetic patients which do not undergo hemodialysis.

The term "intra-cellular domain of the ζ chain" refers to the cytoplasmic portion of the subunit (CD247) of the TCR.

The term "CD3 subunits" refers to gamma, delta, and epsilon CD3 chains (also denoted CD3 γ, δ, or ε).

The term "CD56" refers to an NK cell marker. CD56+ CD3− cells represent NK cells and CD56+CD3+ cells indicate NKT cells.

In the context of the present invention, the term "metabolic diseases" generally refers to diabetes, obesity and cardiovascular diseases.

The term "diabetes" refers to Type I or Type II diabetes and to pregnancy related diabetes.

The term "whole blood" in accordance with the invention refers to blood that has not been fractionated, and from which no constituent such a red blood cells, white blood cells, plasma or platelets has been removed. As used herein the term "blood" refers to whole blood but may also refer to cell-containing fraction of the blood and in particular to a T-lymphocyte, NK and NKT containing fraction. Without wishing to be bound by theory, use of whole blood to determine immunosuppression is advantageous over the use of isolated lymphocytes, since isolation of the lymphocytes from the inflammatory environment may lead to recovery of the abnormal phenotype of the T cells (depending on the severity of the abnormality) thereby leading to false analysis of the patient's condition.

The term "ζexpression level" refers to the level of expression of the ζ chain mRNA or protein, preferably this term refers to the protein level.

The term "ζ selective downregulation of chain expression" refers to a reduction in ζ chain expression levels while the expression of other CD3 subunits remains constant or unchanged. Such selective downregulation is indicative of immunosuppression in the tested subject which is associated with chronic inflammation.

The term "the level of one of the CD3 subunits" refers to the level of expression of the CD3 γ, CD3δ, or CD3ε subunits and encompasses both mRNA and protein expression level, preferably the protein expression level.

The protein expression level may be determined by using anti-ζ chain antibodies, anti-CD3γ, CD3δ, or CDε antibodies and anti-CD56 antibodies. The antibodies are preferably monoclonal. The detection of antibody binding is performed using FACS (as will be explained below) or by any known immuno-detection technique.

By a preferred embodiment the detection of the labeled antibody is by semi-quantitative flow cytometry assay using fluorochrome-labeled monoclonal antibody (mAb) directed against the ζ chain and any of the CD3 chains By a more preferred embodiment the blood cells are fixed and permeabilized before the determination as will be explained in more detail below.

In accordance with the invention the "cells" in which the level of expression is tested are T-lymphocytes, Natural Killer T—(NKT) cells and Natural Killer (NK) cells. Typically the cells are characterized as CD3+CD56− (T cells), CD3+CD56+ natural killer T cells (NKT cells) and CD56+ CD3 (NK cells). Most preferably the tested cells are T cells (CD3+CD56).

The term "diabetes-associated complication" refers both to acute complications of diabetes (such as hypoglycemia, ketoacidosis or nonketotic hyperosmolar coma) or chronic complications of the disease that include cardiovascular disease, chronic renal failure, retinal damage, nerve damage, numb foot), and microvascular damage, which may cause impotence and poor healing of wounds that may result in gangrene.

The unique kit and method of the present invention can be used for any application where the level of the ζ chain needs to be determined including for research purposes, for the diabetes related purposes indicated above as well as for the purposes stipulated in prior application WO05025310 for the detection of an immunosuppressive environment, for example during chronic inflammation, cancer, infections and autoimmune disorders.

A unique feature of the method is that whole blood is used instead of a lymphocyte-containing blood fraction separated for example by Ficoll separation. Thus, use of whole blood provides a more reliable evaluation of the functional properties of T cells in the context of the entire blood cells and factors without changing/separating the cells. Separated T cells could change their phenotype; recover ζ chain expression and function due to their separation from the inflammatory environment (immunosuppressive cells and factors). Moreover, analyzing whole blood samples is easy to perform and also labor and cost saving.

EXAMPLES

1. Measurement of ζ-chain Expression and Cell Subset Immunophenotyping

Blood samples obtained from Type II diabetes patients were subjected to immunophenotyping to analyze distribution of various immune cell subpopulations. ζ chain expression levels were also tested in these blood samples. A minute amount of a whole blood sample (fresh or frozen) is used for the analysis and the read out system is based upon FACS analysis. The experiment was performed as follows:

A semi-quantitative flow cytometry assay using fluorochrome-labeled monoclonal antibody (mAb) directed against the intracytoplasmatic region of the ζ chain (CD247) was used for the analysis. A whole blood sample (as little as 50 µl) was fixed using formaldehyde and permeabilized using a saponin-based solution to allow access of the anti-ζ mAb to the intracytoplasmatic region of the ζ chain.

In addition, lymphocytes were stained using antibodies directed against cell surface expressed proteins and/or total proteins such as CD3, and CD56, which identify different cell subsets, namely T cells and NK cells, respectively. The fixation and permeabilization are crucial steps, which have been performed under optimized conditions. The assay could be performed immediately or several days/months following the receipt of the blood samples, since the whole blood samples (as little as 100µ) can be frozen while preserving their protein expression levels, cell content, viability, and distribution as in the fresh sample. The sample is frozen by mixing one volume of whole blood with one volume of freezing buffer (80% fetal calf serum (FCS), 20% DMSO (dimethyl sulfoxide)).

Briefly, 50-100 microliters of whole blood were fixed (2% paraformaldehyde in 1×PBS for 20 min at 4° C.), washed with PBS and permeabilized (0.1% saponin, 1% Human serum in 1×PBS for 10 minutes at room temperature). The cells were then stained with anti-ζ, anti-CD3ε and anti-CD56 antibodies labeled with different fluorescent dyes as follows: Antibodies were resuspended in permeabilization buffer and mixed with the cells for 30 min at 4° C. Following washes, the samples were resuspended in FACS buffer (1.5% FCS, 0.05% azide in 1×PBS) and analyzed using FACS and the expression of the tested proteins was evaluated according to the obtained mean fluorescence. The antibodies used are commercially available and are manufactured by various companies, for example: Anti-CD3 APC/FITC (BD Pharmingen), Anti-CD56 PE/APC (Dako) and Anti-CD3-ζ FITC/PE (Santa Cruz Biotecnology).

Figure 1G:
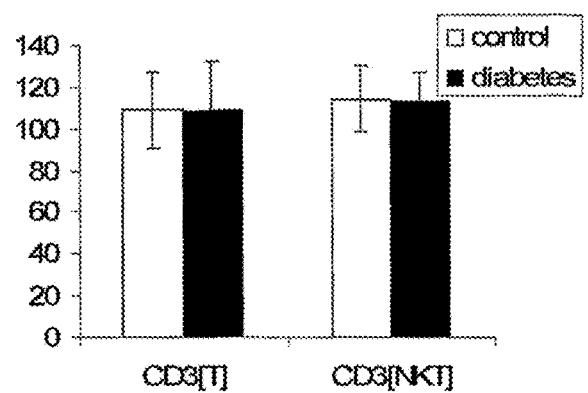
In FIG. 1G CD3ε expression levels were measured by FAGS as MFI within T and NKT cells derived from diabetes patients relative to healthy donors.
Figure 1H:
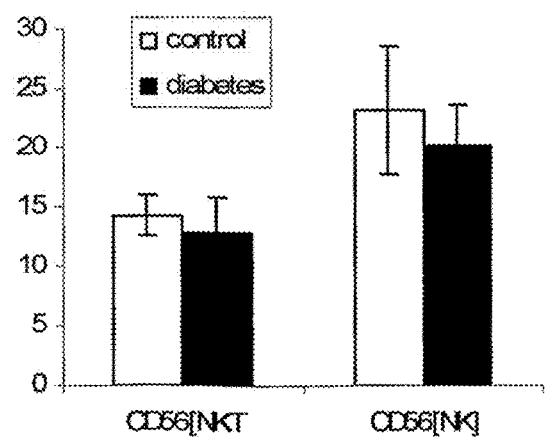
In FIG. 1H CD56 expression levels were measured by FACS as MFI within NKT and T cells derived from diabetes patients relative to healthy donors.

2. Decreased Chain Expression in T, NKT and NK Cells in Type II Diabetes Patients Quantitative measurement of ζ chain expression in different lymphocyte subpopulations such as CD3+CD56− (T cells), CD3+CD56+ natural killer T cells (NKT cells) and CD56+CD3− (NK cells) was performed by measuring mean fluorescence intensity (MFI). The analysis was performed after setting the lymphocyte gate (FCS/SSC) and back-gating on CD3+, CD56+ cells (FIG. 1A). Twenty Type II diabetes patients and six healthy donors (controls) were screened. A significantly decreased MFI for expression was observed within T, NKT and NK cells in the diabetes patients relative to the healthy donors (FIG. 1C-1F). A statistical significant ζ-chain down-regulation was observed within T, NK and NKT cells derived from diabetes patients relative to healthy donors. The results are presented as the mean value of ζ-chain expression within diabetes patients (n=20) and healthy donors (n=6) and standard deviations are shown. *, P<0.0002, P<0.007, *P<0.035 (student T test). As seen in FIG. 1D-1F, while in most of the patients' T, NKT, and NK cells, ζ expression levels were significantly lower than those of the controls, some of the patients displayed normal levels of ζ expression in T (3/20), NK (3/20) and NKT (4/20). When the expression levels of other proteins such as CD3ε and CD56 were compared between samples of healthy donors and Type II diabetes patients, no significant difference was observed (FIG. 1G-1H). Thus, ζ expression appears to be a potential biomarker for monitoring the immune status within diabetes Type II patients. As shown here, ζ expression is affected in all three cell-types (T lymphocytes, NKT and NK cells).

3. Prognostic Importance of the Chain Expression in Type II Diabetes Patients

Presently, inflammatory state in diabetes patients is clinically characterized by measurements of CRP levels and blood sedimentation rate, although CRP levels cannot distinguish between acute and chronic inflammation.

Figure 2A:
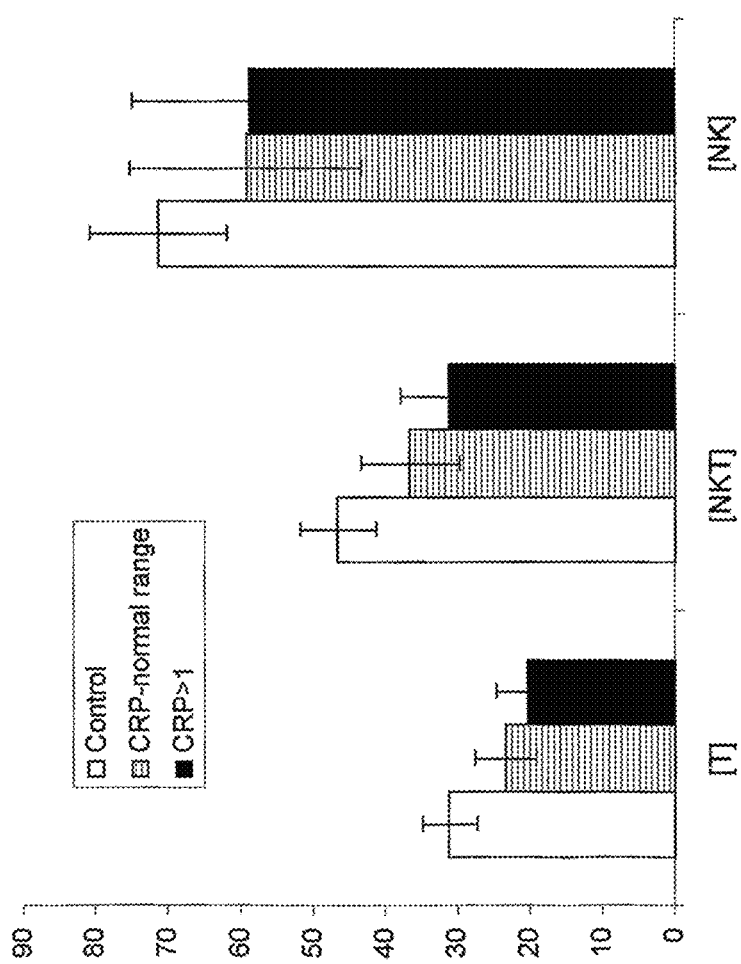
In FIG. 2A ζ-chain expression was measured by FACS as the mean fluorescent intensity (MFI) within each of the cell subsets (T, NKT and NK cells). The results are presented as the mean value of ζ-chain expression of control and diabetic patients with normal [CRP<1] and abnormal [CRP>1] CRP levels and standard deviations are shown. P value is indicated.
Figure 2E:
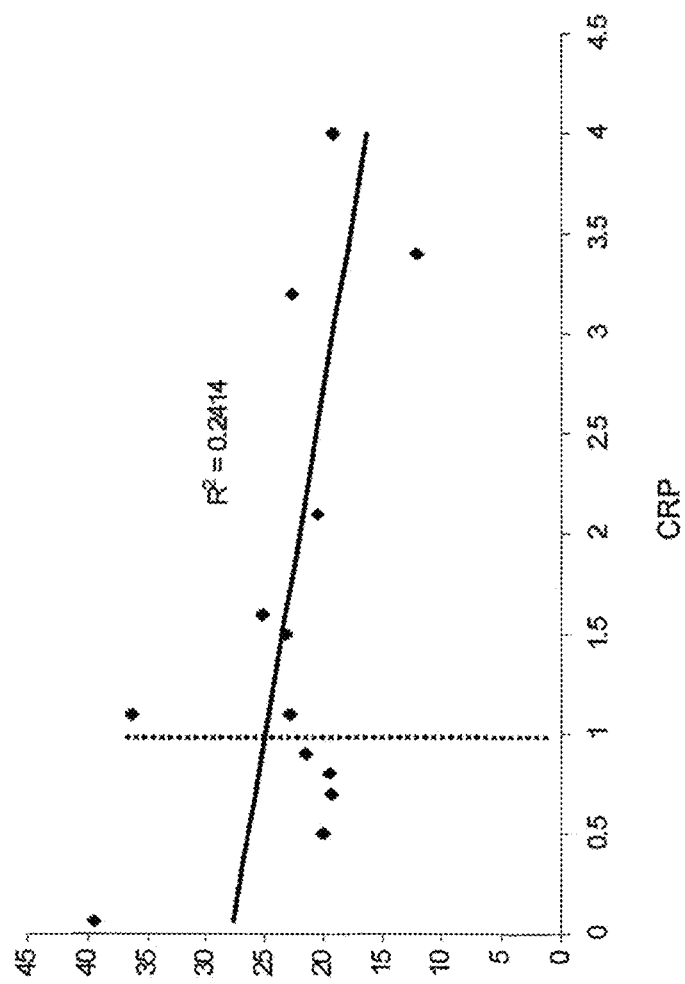
FIG. 2E illustrates the correlation between CRP to ζ-chain expression levels (dotted line indicate barrier of normal CRP levels).

In order to assess whether ζ down-regulation correlates with high CRP levels (CRP>1) in Type II diabetes patients, a correlation assessment was performed. In a retrospective study, Type II diabetes patients were categorized based on their CRP expression levels. Next, ζ chain expression levels were compared between Type II diabetes patients exhibiting normal levels of CRP [CRP<1] and abnormal levels of CRP [CRP>1]. The results indicate that in patients with normal CRP level [CRP<1] significant (P<0.014) low levels of ζ chain were observed in T cells (while in NK and NKT cells ζ expression levels were similar between the patients and the normal controls) (FIG. 2A). However, when individual patients were plotted (FIG. 2B), the majority of the patients expressed reduced ζ chain levels relative to control (FIG. 2B-2D; circled). Thus, although levels of CRP were normal, ζ chain was down regulated. When analyzing the patients with abnormal CRP levels [CRP>1] it appears that these patients exhibit a significant reduction in ζ chain expression in T and NKT (P<0.0002, P<0.0004, respectively) (FIG. 2A). However, when individual patients in this group were plotted there were patients that expressed higher levels of ζ, as in the controls (FIG. 2B-2D; rectangular). Moreover, when CRP levels were compared to ζ chain expression levels, a very low correlation index was calculated (Pearson=0.49) (FIG. 3C). Thus, while CRP serves as a biomarker for inflammation it cannot predict acute vs. chronic inflammation and thus, it might not predict the immunosuppresion or chronic inflammation status of an individual as ζ chain expression level could.

It is important to note that low levels of ζ expression were observed in patients with normal levels of CRP, which based upon CRP measurements are supposed to present characteristics of normal individuals. One of these patients is a woman diagnosed with diabetes Type II that is not receiving any anti-inflammatory treatment and arrived to the emergency room due to vertigo. At this stage, based on the observed ζ chain down regulation, the physician should consider giving the patient anti-inflammatory medications to avoid deterioration of the patient's health conditions due to the fact that low expression levels indicate a state of immunosuppression due to chronic inflammation. Moreover, measurements of ζ expression levels during treatment could be valuable for the evaluation of the efficacy and suitability of the given treatment.

The rest of the patients with normal levels of CRP and ζ down regulation, were Type II diabetes patients that suffer from complications and are receiving various anti-inflammatory medications. The fact that ζ expression in these patients is down regulated may suggest that the medications that these patients are receiving are not suitable and their change should be considered due to the existing immunosuppression. Again, measurements of ζ expression could indicate whether the medical stage of these patients is recovering due to the treatment.

These results suggest that measurements of ζ expression seem to provide an additional parameter that is missed by measurements of CRP. The borderline patients in which CRP levels were normal but chain ζ expression levels were down regulated reflect this conclusion. Again, while CRP serves as a biomarker for inflammation it might not predict the immunosuppression or chronic inflammation status of an individual as ζ chain expression level could.

4. Decreased ζ Expression in Type I Diabetes Patients

Peripheral blood lymphocytes (PBLs) from healthy donors and patients with Type 1 diabetes were analyzed for total ζ and CD3 expression levels by flow cytometry (FACS). The white blood cells were separated from the whole blood using FICOLL-HYPAQUE™. The samples were fixed, permeabilized, stained with anti-ζ, and anti-CD3 antibodies and analyzed by FACS. Ficoll is a neutral, highly branched, high-mass, hydrophilic polysaccharide and Hypaque is sodium metrizoate. "FICOLL-TYPAQUE™" is also a density-gradient centrifugation technique for separating peripheral blood mononucleated cells such as lymphocytes, from other formed elements in blood.

Figure 3A:
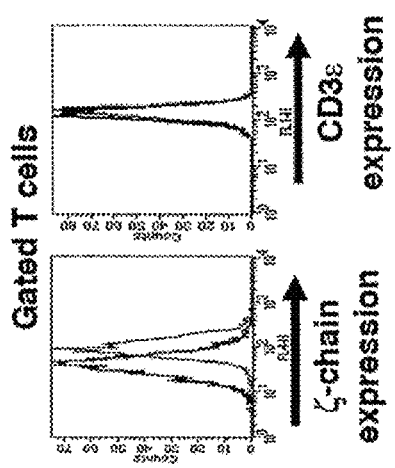
FIGS. 3A-3C are graphic representations showing ζ chain expression as a biomarker in Type 1 diabetes patients.
Figure 3B:
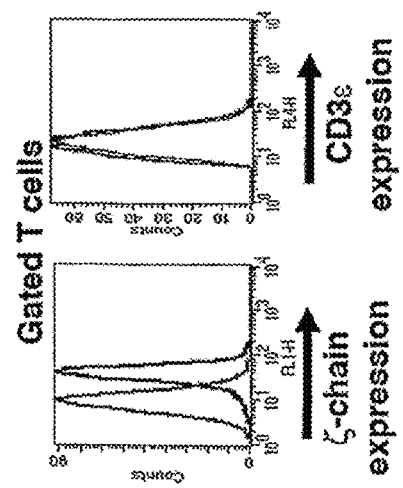
Figure 3C:
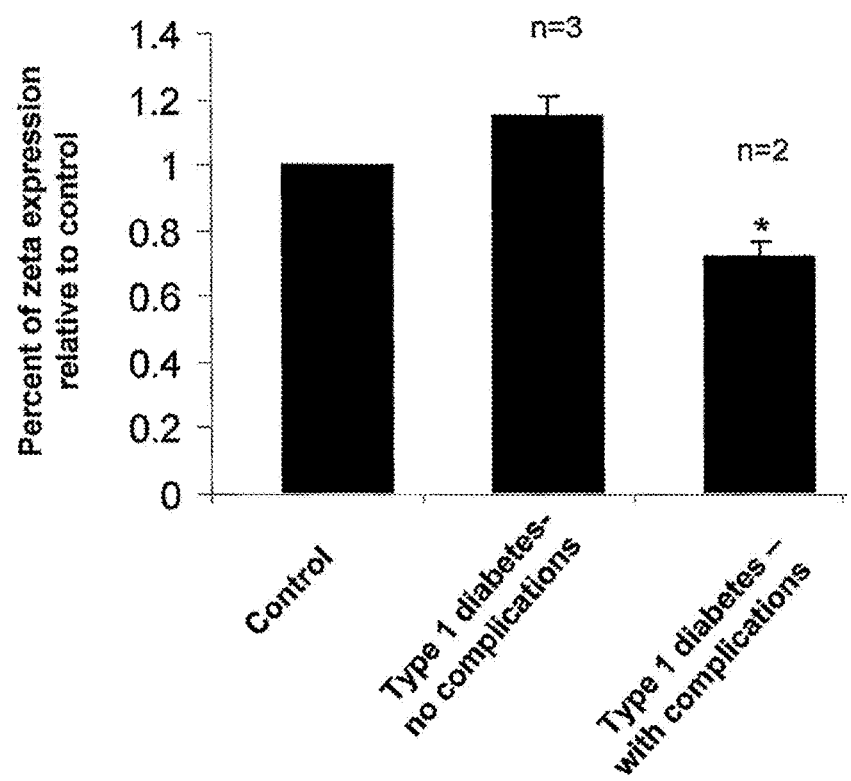

Two Type I diabetes patients were analyzed and a significant decrease of MFI for ζ chain was observed while CD3ε chain expression levels remained the same (FIG. 3A, B).

To identify whether ζ chain expression level might serve as a biomarker and distinguish between patients with or without complications, usually occurring due to the developing chronic inflammation, ζ expression was analyzed in three Type I patients without complications and two Type I patients with complications. Whole fresh blood samples from healthy donors (controls) and patients exhibiting Type 1 diabetes with (n=2) or without (n=3) complications were used for the experiment.

The results indicate that Type I diabetes patients with complications show a significant reduced ζ expression relative to Type I diabetes patients with no complications and to control donors (FIG. 3C). A statistical significant ζ chain down-regulation was observed in the patients exhibiting Type 1 diabetes with complications relative to the healthy donors (controls) and the patients exhibiting Type 1 diabetes with no complications. *, P<0.02 (student T test). These results indicate that ζ chain expression level could serve as a biomarker and distinguish between diabetic patients with or without complications which usually occur due to the developing chronic inflammation.

5. Measurements of T Cell Functions in Diabetic Patients

Various additional parameters could indicate an immunosuppression including impaired proliferation of T-cells following activation via the TCR, reduced levels of induced activation markers such as CD25 and cytokine production such as IL2, IFNγ, TNFα and IL6, upon TCR mediated T cell activation.

Figures 4A, 4B:
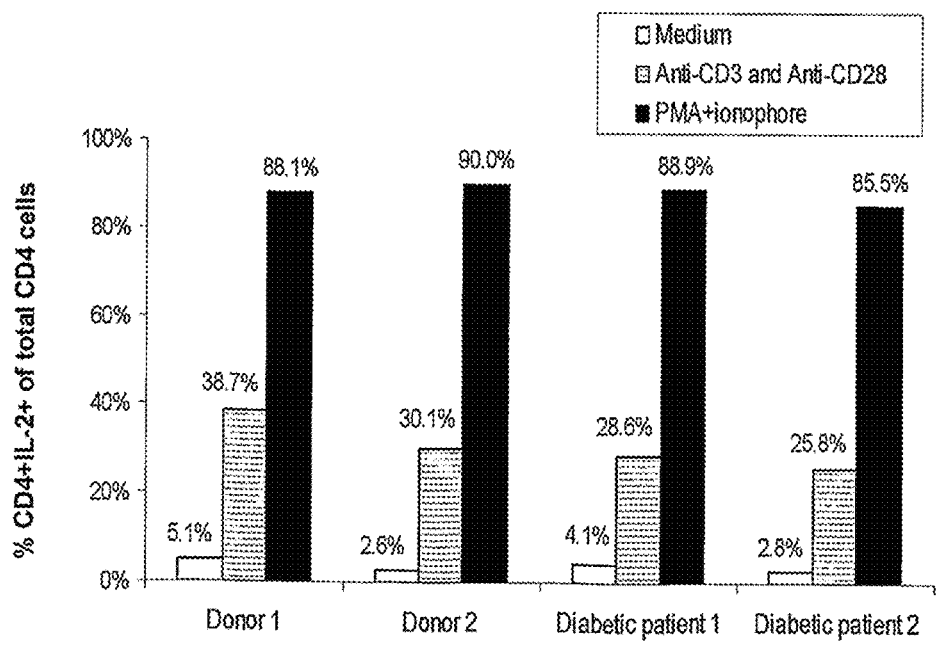
FIG. 4B illustrates FACS analysis for total IL-2 expression within the gated CD4+ T cells.

In order to determine the correlation between zeta expression and T cell function in diabetic patients several parameters were measured. First, whole blood samples from healthy donors and diabetic patients were analyzed for total ζ chain (using CD247) and CD3ε expression levels (FIG. 4A). Leukocytes from total blood of healthy donors and diabetic patients were activated for 12 hr in the presence of monensin with anti-CD3 and anti-CD28 antibodies or with phorbol ester acetate (PMA) and $Ca^{2+}$ ionophore or left untreated. Gated CD4 T cells from diabetic patients, which were stimulated via the TCR or with a combination of PMA and $Ca^{2+}$ ionophore that bypass TCR-mediated activation, showed no significant difference (P<0.12) in IL-2 expression to those of T cells derived from healthy donors (FIG. 4B).

Figure 4C:
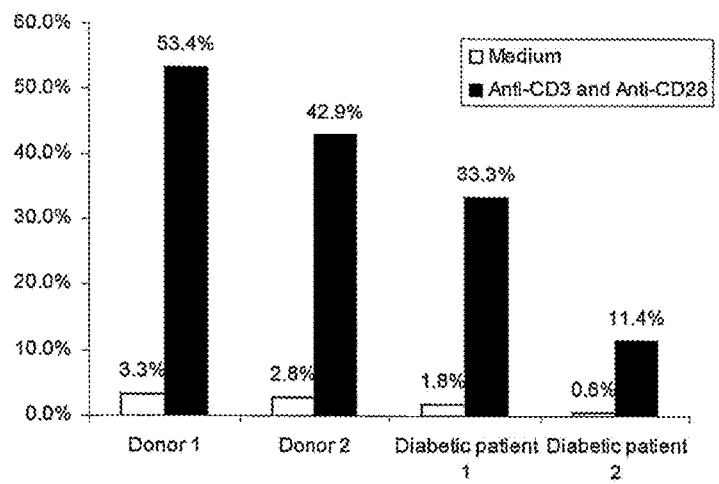
In FIG. 4C leukocyte from total blood of healthy donors and diabetic patients were activated as in FIG. 4B for 12 hours, and analyzed by FACS for surface expression of CD25 within gated CD4+ T cell population.
Figures 4D, 4E:
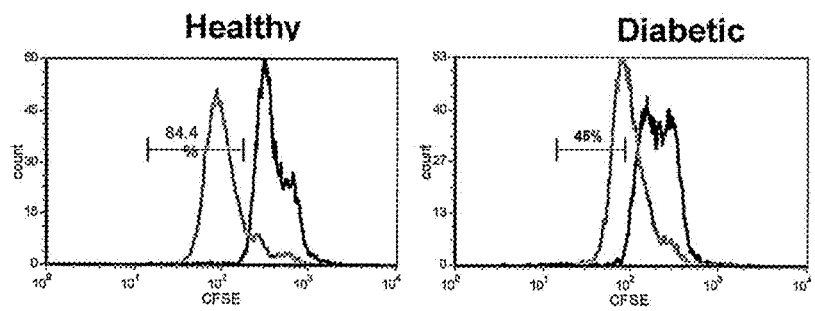
In FIGS. 4D 4e, 4F and 4G leukocytes from healthy donors and diabetic patients were labeled with CFSE and then activated as in (B) for 72 hours (red histograms) or left untreated with medium (black histograms). The proliferative response was assessed according to the percentage of the divided cells of gated CD4+ T cells.
Figures 4F, 4G:
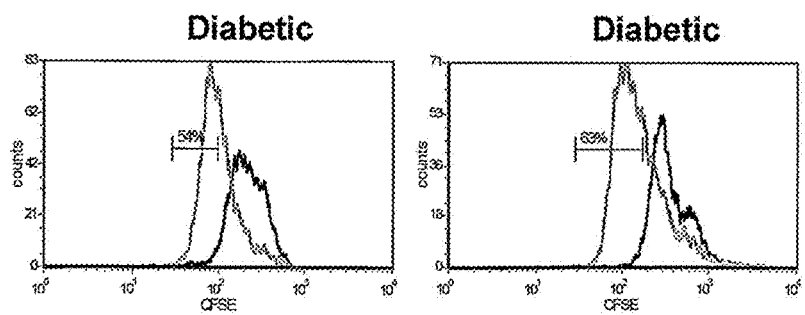

However, Gated CD4 T cells from diabetic patients with reduced zeta chain expression showed significant (P<0.04) lower expression levels of surface CD25 (FIG. 4C) and impaired T cell proliferation (FIG. 4D-4G) upon activation via the TCR.

It should be noted that the tests measuring T cell activation parameters are time consuming and require 12-72 hours. Moreover, changes in these parameters could occur also due to causes other than immunosuppression-induced chronic inflammation. In contrast, measuring zeta expression combined with CD3 and/or CD56 expression levels, provides indication of chronic inflammation-induced immunosuppression; namely, low zeta expression levels and constant (i.e. unchanged) CD3 and/or CD56 expression levels. T cell proliferation, activation markers, and cytokine production could only add additional support of an immunosuppression state.

BIBLIOGRAPHY

1. Baniyash M. Down-regulation of the TCR chain ζ curtailing an excessive inflammatory immune response. Invited review for *Nat. Immunol. Rev.* (2004) 4:675-687.
2. Bronstein-Sitton N., Cohen-Daniel L., Vaknin I., Ezernitchi A V., Leshem B., Halabi A., Houri-Hadad Y., Greenbaum E., Zakay-Rones Z., Shapira L., and Baniyash M. Sustained exposure to bacterial antigen induces IFNγ-dependent T cell antigen receptor zeta down-regulation and impaired T cell function. *Nat. Immunol.* (2003) 4:957-964.

3. Ezernitchi, A. V., Vaknin I, Cohen-Daniel, L., Levy, O., Halabi, A., Pikarsky, E., Shapira, L. and Baniyash, M. TCR zeta, down-regulation under chronic inflammation is mediated by myeloid suppressor cells differentially distributed between various lymphatic organs. *J. Immunol.* (2006) 177:4763-72.
4. Vaknin, I., Blinder, L., Wang, L., Gazit, R., Shapira, E., Genina, O., Pines, M. Pikarsky, E. and Baniyash M. A common pathway mediated through Toll-like receptors leads to T and natural killer cell immunosuppression. *Blood* (2008) 111:1437-47.
5. Eleftheriadis T, Kartsios C, Yiannaki E, Kazila P, Antoniadi G, Liakopoulos V, Markala D. Chronic inflammation and T cell zeta-chain downregulation in hemodialysis patients. Am J Nephrol. (2008). 28:152-7.
6. Nambiar M P, Enyedy E J, Fisher C U, Krishnan S, Warke V G, Gilliland W R, Oglesby R J, Tsokos G C. Abnormal expression of various molecular forms and distribution of T cell receptor zeta chain in patients with systemic lupus erythematosus. *Arthritis Rheum.* (2002). 46:163-74.
7. Kuss I, Saito T, Johnson J T, Whiteside T L. Clinical significance of decreased zeta chain expression in peripheral blood lymphocytes of patients with head and neck cancer. *Clin Cancer Res.* (1999) 5:329-34.
8. Hotamisligil S G, Inflammation and metabolic disorders. *Nature* (2006) 444:860-867.
9. Harrison's principles of internal medicine. 16 ed, ed. A. S. F. Dennis L Kasper, Dan L Longo, Eugene Braunwald, Stephen L. Hauser, J. Larry Jameson. (2005) McGraw-Hill Companies, Inc.
10. Wang A Y. Prognostic value of C-reactive protein for heart disease in dialysis patients. *Curr Opin Investig Drugs* (2005). 6:879-86.
11. Nanri A, Moore M A, Kono S Impact of C-reactive protein on disease risk and its relation to dietary factors. *Asian Pac J Cancer Prev.* (2007) 8:167-77.
12. Eisenbarth, G. S. and M. Stegall, Islet and pancreatic transplantation-autoimmunity and alloimmunity N Engl J Med, (1996). 335: 888-90.
13. Boden, G. and M. Laakso, Lipids and glucose in type 2 diabetes: what is the cause and effect? *Diabetes Care*, (2004) 27:2253-9.
14. Eldor, R. and I. Raz, Lipids and glucose in type 2 diabetes: what about the beta-cell and the mitochondria?: response to Boden and Laakso. *Diabetes Care* (2005) 28:985-6; author reply 986-7.
15. Tsirpanlis, G., Inflammation in atherosclerosis and other conditions: a response to danger. *Kidney Blood Press Res* (2005) 28: 211-7.
16. Pickup, J. C., Inflammation and activated innate immunity in the pathogenesis of type 2 diabetes. Diabetes Care (2004) 27:813-23.
17. Schalkwijk, C. G., et al., Plasma concentration of C-reactive protein is increased in type I diabetic patients without clinical macroangiopathy and correlates with markers of endothelial dysfunction: evidence for chronic inflammation. *Diabetologia*, (1999) 42:351-7.
18. Schram, M. T., et al., Markers of inflammation are cross-sectionally associated with microvascular complications and cardiovascular disease in type 1 diabetes—the EURODIAB Prospective Complications Study. *Diabetologia* (2005) 48:370-8.

What is claimed is:

1. A method for determining diabetes complications in a diabetic patient, the method comprising:
    drawing blood from the patient to obtain a blood sample;
    measuring an expression level of an intracellular domain of a ζ chain in cells of the patient blood sample comprising detecting in vitro an amount of the intracellular domain of the ζ chain in the cells;
    measuring an expression level of at least one CD3 subunit in the cells, comprising detecting in vitro an amount of CD3 subunit in the cells;
    measuring an expression level of at least one specific NK cell marker in the cells comprising detecting in vitro an amount f NK cell marker in the cells; and
    comparing the expression level of each of the intracellular domain of the ζ chain, at least one CD3 subunit, and at least one specific NK cell marker, to a corresponding normal standard expression level, for each of the intracellular domain of the ζ chain, at least one CD3 subunit, and at least one specific NK cell marker, respectively,
    wherein an expression level of the intracellular domain of the ζ chain in the sample that is significantly below the normal standard, and the normal standard expression level of the at least one CD3 subunit and the at least one specific NK cell marker, indicates the presence of diabetes complications in the diabetic patient; and
    treating the diabetic patient suffering from diabetes complications based on the measured expression levels of the intracellular domain of the ζ chain, the at least one CD3 subunit and the at least one specific NK cell marker, by administering to the diabetic patient a therapeutically effective amount of a pharmaceutical composition that treats the diabetes complications, wherein said therapeutically effective amount raises the expression level of the intracellular domain of the ζ chain in the diabetic patient such that it is not significantly below the corresponding normal standard.

2. The method according to claim 1, wherein measuring the expression level of an intracellular domain of the ζ chain in cells of the patient blood sample comprises detecting in vitro the amount of the intracellular domain of the ζ chain in the cells.

3. The method of claim 1, wherein the at least one specific NK cell marker is CD56.

4. The method of claim 1, wherein treating comprises inhibiting the activity of CD11b+Gr1+ myeloid derived suppressor cells in the patient.

5. The method of claim 1, wherein the diabetes complications are diabetes-related or diabetes-associated, and comprise one or more of hypoglycemia, ketoacidosis, nonketotic hyperosmolar coma, cardiovascular disease, cerebrovascular disease, chronic renal failure, retinal damage, nerve damage, numb foot, vascular injury, microvascular damage, impotence, poor wound healing, gangrene; and systemic inflammation.

6. The method of claim 1, wherein the diabetes complications are diabetes-related or diabetes-associated, and comprise one or more of hypoglycemia, ketoacidosis, nonketotic hyperosmolar coma, cardiovascular disease, cerebrovascular disease, retinal damage, nerve damage, numb foot, impotence, poor wound healing, gangrene, and systemic inflammation.

7. A method for determining diabetes complications in a diabetic patient, the method comprising:
    drawing blood from the patient to obtain a blood sample;
    measuring an expression level of an intracellular domain of ζ chain in cells of the patient blood sample comprising detecting in vitro an amount of the intracellular domain of the ζ chain in the cells;

measuring an expression level of at least one CD3 subunit in the cells, comprising detecting in vitro an amount of CD3 subunit in the cells;

measuring an expression level of at least one specific NK cell marker in the cells comprising detecting in vitro an amount of NK cell marker in the cells; and comparing the expression level of each of the intracellular domain of the ζ chain, at least one CD3 subunit, and at least one specific NK cell marker, to a corresponding normal standard expression level, for each of the intracellular domain of the ζ chain, at least one CD3 subunit, and at least one specific NK cell marker, respectively, wherein an expression level of intracellular domain of the ζ chain in the sample that is significantly below the normal_standard, and the normal standard expression level of the at least one CD3 subunit and the at least one specific NK cell marker, indicates the presence of diabetes complications; and if diabetes complications are indicated in the diabetic patient, treating the diabetic patient suffering from diabetes complications based on the measured expression levels of the intracellular domain of the ζ chain, the at least one CD3 subunit and the at least one specific NK cell marker, by administering to the diabetic patient a therapeutically effective amount of a pharmaceutical composition that treats diabetes complications, wherein said therapeutically effective amount raises the expression level of the intracellular domain of the ζ chain in the diabetic patient such that it is not significantly below the corresponding normal_standard.

8. The method of claim 7, wherein the at least one specific NK cell marker is CD56.

9. The method of claim 7, wherein treating comprises inhibiting the activity of CD11b+Gr1+ myeloid derived suppressor cells in the patient.

10. The method of claim 7, wherein the diabetes complications are diabetes-related or diabetes-associated, and comprise one or more of hypoglycemia, ketoacidosis, nonketotic hyperosmolar coma, cardiovascular disease, cerebrovascular disease, chronic renal failure, retinal damage, nerve damage, numb foot, vascular injury, microvascular damage, impotence, poor wound healing, gangrene, and systemic inflammation.

11. The method of claim 7, wherein the diabetes complications are diabetes-related or diabetes-associated, and comprise one or more of hypoglycemia, ketoacidosis, nonketotic hyperosmolar coma, cardiovascular disease, cerebrovascular disease, retinal damage, nerve damage, numb foot, impotence, poor wound healing, gangrene, and systemic inflammation.

12. A method for determining diabetes complications in a diabetic patient, the method comprising:

drawing blood from the patient to obtain a whole blood sample;

contacting the whole blood sample with a fixating agent thereby fixing the cells in the whole blood sample to produce fixed cells;

permeabilizing the fixed cells to produce permeabilized cells;

measuring an expression level of an intracellular domain of an ζ chain in cells of the patient whole blood sample comprising contacting the permeabilized cells with antibodies directed against an intra-cellular domain of the ζ chain and detecting in vitro antibody-ζ chain complexes;

measuring an expression level of at least one CD3 subunit in the cells, comprising contacting the permeabilized cells with antibodies directed against at least one CD3 subunit and detecting in vitro antibody-CD3 subunit complexes;

measuring an expression level of at least one specific NK cell marker in the cells comprising contacting the permeabilized cells with antibodies directed against at least one specific NK cell marker and detecting in vitro antibody-NK cell marker complexes; and comparing the expression level of each of the intracellular domain of the ζ chain, at least one CD3 subunit, and at least one specific NK cell marker, to a corresponding normal standard expression level, for each of intracellular domain of the ζ chain, at least one CD3 subunit, and at least one specific NK cell marker, respectively, wherein an expression level of the intracellular domain of the ζ chain in the sample that is significantly below the normal standard, and the normal standard expression level of the at least one CD3 subunit and the at least one specific NK cell marker, indicates the presence of diabetes complications; and treating the diabetic patient suffering from diabetes complications based on the measured expression levels of the intracellular domain of the ζ chain, the at least one CD3 subunit and the at least one specific NK cell marker by administering to the diabetic patient a therapeutically effective amount of a pharmaceutical composition that treats diabetes complications; wherein said therapeutically effective amount raises the expression_level of the intracellular domain of the ζ chain in the diabetic patient such that it is not significantly below the corresponding normal_standard.

13. The method of claim 12, wherein the at least one specific NK cell marker is CD56.

14. The method of claim 12, wherein the antibodies directed against an intra-cellular domain of the ζ chain, the antibodies directed against at least one CD3 subunit, and the antibodies directed against at least one specific NK cell marker, are each labeled with a detectable label.

15. The method of claim 14, wherein said antibodies are labeled with biotin or a fluorescent dye.

16. The method of claim 12, wherein said expression levels are measured using labeled antibodies.

17. The method of claim 12, wherein treating comprises inhibiting the activity of CD11b+Gr1+ myeloid derived suppressor cells in the patient.

18. The method of claim 12, wherein the diabetes complications are diabetes-related or diabetes-associated, and comprise one or more of hypoglycemia, ketoacidosis, nonketotic hyperosmolar coma, cardiovascular disease, cerebrovascular disease, chronic renal failure, retinal damage, nerve damage, numb foot, vascular injury, microvascular damage, impotence, poor wound healing, gangrene, and systemic inflammation.

19. The method of claim 12, wherein the diabetes complications are diabetes-related or diabetes-associated, and comprise one or more of hypoglycemia, ketoacidosis, nonketotic hyperosmolar coma, cardiovascular disease, cerebrovascular disease, retinal damage, nerve damage, numb foot, impotence, poor wound healing, gangrene, and systemic inflammation.

* * * * *